US012648915B2

(12) United States Patent
Sun et al.

(10) Patent No.: US 12,648,915 B2
(45) **Date of Patent: *Jun. 9, 2026**

(54) SYNERGISTIC ANTI-VIRAL PHARMACEUTICAL COMPOSITION CONTAINING TARGETING NANOPARTICLES

(71) Applicant: Nuecology Biomedical Inc., Richmond (CA)

(72) Inventors: Chung Chin Sun, Richmond (CA); Dean Mo Liu, Surrey (CA)

(73) Assignee: NUECOLOGY BIOMEDICAL INC., Richmond (CA)

( * ) Notice: Subject to any disclaimer, the term of this patent is extended or adjusted under 35 U.S.C. 154(b) by 714 days.

This patent is subject to a terminal disclaimer.

(21) Appl. No.: 17/926,663

(22) PCT Filed: May 24, 2021

(86) PCT No.: PCT/CA2021/050699

§ 371 (c)(1),
(2) Date: Nov. 21, 2022

(87) PCT Pub. No.: WO2021/232169

PCT Pub. Date: Nov. 25, 2021

(65) Prior Publication Data

US 2023/0233473 A1 Jul. 27, 2023

Related U.S. Application Data

(60) Provisional application No. 63/028,958, filed on May 22, 2020.

(51) Int. Cl.

| | |
|---|---|
| ***A61K 9/51*** | (2006.01) |
| ***A61K 9/00*** | (2006.01) |
| ***A61K 31/12*** | (2006.01) |
| ***A61K 31/706*** | (2006.01) |
| ***A61K 45/06*** | (2006.01) |

(52) U.S. Cl.

CPC .............. *A61K 9/51* (2013.01); *A61K 9/0019* (2013.01); *A61K 31/12* (2013.01); *A61K 31/706* (2013.01); *A61K 45/06* (2013.01)

(58) Field of Classification Search

CPC ........ A61K 9/51; A61K 9/0019; A61K 31/12; A61K 31/706; A61K 45/06; B82Y 5/00; A61P 31/12; A61P 31/14

See application file for complete search history.

(56) References Cited

U.S. PATENT DOCUMENTS

2014/0162888 A1* 6/2014 Kuslich ................ C12Q 1/6886 506/9

FOREIGN PATENT DOCUMENTS

| | | | |
|---|---|---|---|
| CA | 2 621 641 A1 | 3/2007 | |
| CN | 111171078 B * | 4/2022 | ............ C07F 9/6561 |

OTHER PUBLICATIONS

Raja et al. (Current Drug Delivery, 2015, 12, 613-627) (Year: 2015).*

Klinger et al., Therapeutic Potential of Curcumin for the Treatment of Brain Tumors, Oxidative Medicine and Cellular Longevity, vol. 2016, Article ID 9324085, 14 pages. (Year: 2016).*

English translation of International S t for International Application No. PCT/CA2021/050699 dated Oct. 18, 2021.

Raja et al., "Nanoparticles Based on Oleate Alginate Ester as Curcumin Delivery System", Current Drug Delivery, vol. 12, 2015, pp. 613-627.

Wang et al., "Remdesivir and Chloroquine Effectively Inhibit the Recently Emerged Novel Coronavirus (2019-nCOV) in Vitro", Cell Research, vol. 30, 2020 (published online Feb. 4, 2020), pp. 269-271.

* cited by examiner

*Primary Examiner* — Sahana S Kaup
*Assistant Examiner* — Abdulrahman Abbas
(74) *Attorney, Agent, or Firm* — Birch, Stewart, Kolasch & Birch, LLP

(57) ABSTRACT

The present disclosure provides a dual-drag-containing nanoparticle, in which a first antiviral drag, such as remdesivir and a second antiviral drag are co-encapsulated and co-delivered by the nanoparticle, said nanoparticle comprising an alginate-oleic acid particle. The disclosure also relates to the therapeutic use of the nanoparticle in treating viral infections, such as SARS-CoV-2.

16 Claims, 2 Drawing Sheets

SYNERGISTIC ANTI-VIRAL PHARMACEUTICAL COMPOSITION CONTAINING TARGETING NANOPARTICLES

CROSS REFERENCE TO RELATED APPLICATIONS

This application is the National Phase of PCT International Application No. PCT/CA2021/050699, filed on May 24, 2021, which claims priority under 35 U.S.C. 119(e) to U.S. Provisional Application No. 63/028,958, filed on May 22, 2020, all of which are hereby expressly incorporated by reference into the present application.

FIELD OF THE INVENTION

The present invention pertains to an anti-virus pharmaceutical composition containing targeting nanoparticles, which provides synergistic efficacy.

BACKGROUND OF THE INVENTION

The treatment of viruses has been a major challenge in clinical practices. Vaccine has recognized as one of the decisive and ultimate means to solve the virus-related diseases in human. Coronavirus such as the case of SARS-CoV-1 outbreak in 2002-2003 and SARS-CoV-2 in 2019-2021. Formally World Health Organization (WHO) named as COVID-19 has threatened the life and living style of human around the world since its outbreak in 2019.

The global pandemic of novel coronavirus disease 2019, COVID-19, caused by severe acute respiratory syndrome coronavirus 2 (SARS-CoV-2) began in Wuhan, China, in December 2019, and has since spread worldwide. As of end of April, 2020, there have been more than 3 million reported cases and more than 230,000 deaths in more than 200 countries. This novel Betacoronavirus is similar to severe acute respiratory syndrome coronavirus (SARS-CoV) and Middle East respiratory syndrome coronavirus (MERS-CoV). Based on its genetic proximity, it likely originated from bat-derived coronaviruses with spread via an unknown intermediate mammal host to humans. The viral genome of SARS-CoV-2 was rapidly sequenced to enable diagnostic testing, epidemiologic tracking, and development of preventive and therapeutic strategies. Currently, there is no strong and clinically-decisive evidence from randomized clinical trials that any potential therapy improves outcomes inpatients with either suspected or confirmed COVID-19.

As a desperate need of a cure or better treatment to against COVID-19 or more generally known as coronaviruses, a number of attempts to use all kinds of potential drugs (included either FDA proven or unproven drugs), such as a second drug comprising of one of the drugs as favipiravir or avigan, hydroxychloroquine, carfilzomib, darunavi, pitavastatin, lamivudine, lopinavir, nelfinavir, ritonavir, darunavir, ledipasvir, telaprevir, rosuvastatin calcium, atovaquone, moexipril, azithromycin, curcumin, dexamethasone, or artemisinin. etc., has been largely explored in different countries in order to effectively slow the spreading rate and more importantly, to reduce or stop mortality rate over current pandemic situation. However, either its poor efficacy in clinical performance or severe side effects that caused a higher death toll as clinically reported. For example, chloroquine and hydroxychloroquine are effective against malaria, rheumatoid arthritis, and lupus, but likely not COVID-19, and caused death due to cardiac side effects, Remdesivir, is a broad-spectrum antiviral medication and as of 2020, remdesivir is being tested as a specific treatment for COVID-19, and has been authorized by the U.S. Food and Drug Administration (FDA) under Emergency Use Authorization (EUA) for emergency treatment for those hospitalized with severe disease. However, it caused severe liver and kidney damage or dysfunction in hospitalized patients. A combination of those above-mentioned drugs has been found some synergistic therapeutic performance, but raised side-effect as well.

There has an emerging and clinically need to find better and synergistic solution to use those drug candidates, either for those aforementioned or not limited to those drugs mentioned above, which included as of autophagy inhibitors, protease inhibitors, antibiotics, or plant drugs.

SUMMARY OF THE INVENTION

Accordingly, the present invention provides a better and synergistic solution to use anti-virus drug candidates encapsulated in AGO particles. As has been well recognized in a number of anti-virus strategies, a combination of drugs with either sequential delivery or co-delivery has received outstanding therapeutic synergy against virus, particularly coronavirus. Along the line, there has been well-known the use of nanotechnology to encapsulate with either single or multiple drugs is expected to largely enhance therapeutic performance and in the meantime, reduce side effect stemmed from toxicity of the free drug itself and excipients used to blend with drug for ease of administration. Therefore, by co-encapsulating and co-delivering of multiple drugs may impart synergistic efficacy against coronavirus, e.g., SARS-CoV-2.

In one aspect, the present invention provide a nanoparticle encapsulating a first anti-virus drug, and a second anti-viral drug; and wherein the first drug and the second drug are encapsulated in an alginate-oleic acid (AGO) particle.

In some examples of the invention, the AGO particle includes a molecule selected from the group consisting of fatty acid-modified alginate salts, and oleic acid-modified alginate, omeg-3-modified alginate, olinic acid-modified alginate.

In one embodiment of the invention, the first anti-virus drug is remdesivir.

In one embodiment of the invention, the second anti-virus drug is an autophagy inhibitor, a protease inhibitor, an antibiotic, or a plant drug.

In one example of the invention, the second anti-virus drug is selected from the group consisting of Favipiravir, Avigan, Hydroxychloroquine, Carfilzomib, Darunavi, Pitavastatin, Lamivudine, Lopinavir, Nelfinavir, Ritonavir, Darunavir, Ledipasvir, Telaprevir, Rosuvastatin Calcium, Atovaquone, Moexipril, Moexipril, Moexipril, Azithromycin, Curcumin, artemisinin and combination thereof.

In one example of the invention, the particle i a remdesivir-curcumin particle.

In one embodiment, the AGO particle is conjugated on the surface of the particle with a human Angiotensin-converting enzyme 2 (ACE2) antibody.

In another aspect, the present invention provides a pharmaceutical composition comprising the particle according to the invention.

In a further aspect, the present invention provides a method for treatment of virus infection in a subject, comprising administering to the subject a pharmaceutical composition according to the invention.

According to the present invention, the particle has a particle size that ranges from 50 nm to 600 nm, more preferably from 50 nm to 300 nm; most preferably 50 nm to 100 nm.

Furthermore, the present invention provides a pharmaceutical composition, comprising the particle described above.

In addition, the present invention provides a method for treatment of a virus infection in a subject, which includes administering to the subject the pharmaceutical composition described above.

In one example of the invention, the virus is a coronavirus, particularly SARS-CoV-2.

The present invention will be further described by way of the following examples. However, it should be understood that the following examples are solely intended for the purpose of illustration and should not be construed as limiting the invention in practice.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
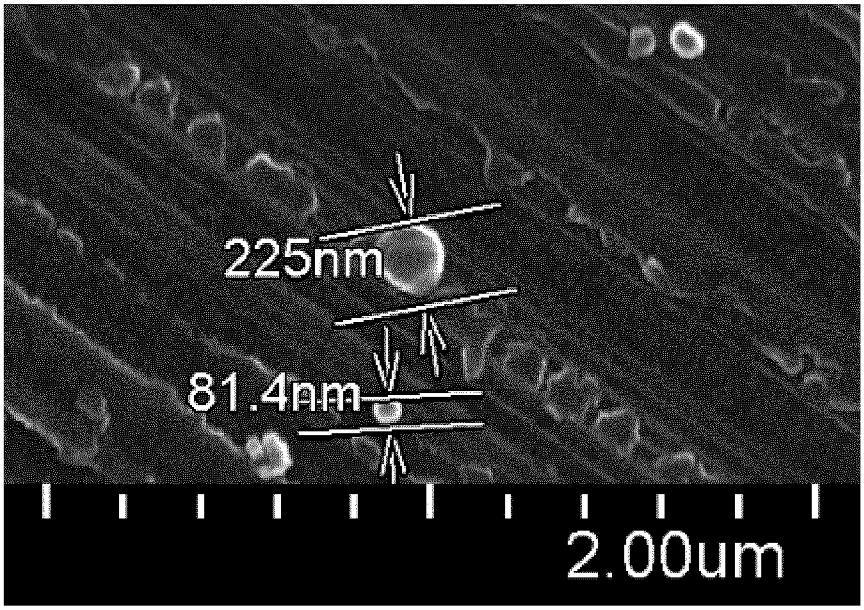
FIG. 1 provides Remdesivir and Dexamethasone released from the dual-drug-carrying AGO nanoparticle, as prepared in Example 4.

Unless defined otherwise, all technical and scientific terms used herein have the same meaning as commonly understood by a person skilled in the art to which this invention belongs.

The present invention provides a dual-drug containing nanoparticle that is designed for antiviral treatment, with or without targeting capability, where the dual drug comprising a first drug, i.e., remdesivir, and a second drug which is selected from one of the group consisting of Favipiravir, Avigan, Hydroxychloroquine, Carfilzomib, Darunavi, Pitavastatin, Lamivudine, Lopinavir, Nelfinavir, Ritonavir, Darunavir, Ledipasvir, Telaprevir, Rosuvastatin Calcium, Atovaquone, Moexipril, Moexipril, Moexipril, Azithromycin, Curcumin, and Artemisinin.

Remdesivir

Remdesivir, which has been recognized as a promising anti-viral drug FDA-approved for emergency use only, is a prodrug that by the action of esterase and phosphoramidase, is converted to GS-441524 mono-phosphate. This in turn is phosphorylated further by nucleotide kinases to triphospho GS-441525. As an adenosine nucleotide triphosphate analog, it interferes with the action of viral RNA-dependent RNA polymerase and evades proofreading by viral exoribonuclease (ExoN), causing a decrease in viral RNA production. In some viruses such as the respiratory syncytial virus, it may cause RNA-dependent RNA polymerases to pause, but its predominant effect (in case of Ebola) is to induce an irreversible chain termination. Unlike many other chain terminators, this is not mediated by preventing addition of the subsequent nucleotide, but is delayed instead, occurring after additional bases have been added to the growing RNA chain. It is also a potential combination of remdesivir with other inhibitors, antibiotics and/or plant drugs such as curcumin by co-encapsulation using a potential polymeric nanoparticle for a subsequent medical purpose.

Other Anti-Virus Drugs

According to the present invention, a second dug may be an autophagy inhibitor, a protease inhibitor, an antibiotic, or a plant drug, which exhibits anti-viral activity. In one embodiment, the second drug is selected from the group consisting of Favipiravir, Avigan, Hydroxychloroquine, Carfilzomib, Darunavi, Pitavastatin, Lamivudine, Lopinavir, Nelfinavir, Ritonavir, Darunavir, Ledipasvir, Telaprevir, Rosuvastatin Calcium, Atovaquone, Moexipril, Moexipril, Moexipril, Azithromycin, Curcumin, Artemisinin and combination thereof. As has been well recognized in a number of anti-cancer strategies, a combination of drugs with either sequential delivery or co-delivery has received outstanding therapeutic synergy to against malignant tumors.

Alginate-Oleic Acid (AGO) Particles

Alginate-oleic acid (AGO) particles, which is also called as "AGO," is a particle made from a new macromolecule as disclosed in PCT/CA2021/050293 filed Mar. 5, 2021, the entire contents of which is hereby incorporated by reference herein. AGO macromolecule is composed of alginate and oleic acid linked with a spacer and an alginate-oleic acid (AGO) particle is formed from the AGO macromolecules. The AGO particles have bio-functionality such as controlled cytocompatibility, controlled degradation (by kidney metabolization), etc., which are introduced into the modified alginates without changing its clinically advantageous properties, e.g., cell-specific compatibility, non-immunogenicity, and structure stability. for its ultimate use in medical practice. As described in PCT/CA2021/050293, alginate is unbranched anionic polysaccharide consisting of 1→4 linked β-D-mannuronic acid (M) and C-5 epimer α-L-guluronic acid (G):

(M)

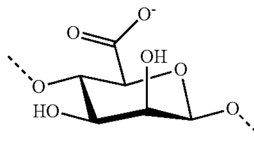

1 → 4 linked β-D-mannuronic acid (G)

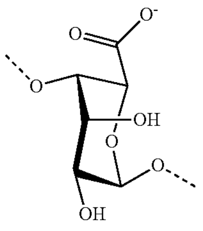

C-5 epimer α-L-guluronic acid

Preparation of Alginate-mOA Nanoparticle (AGO Nanoparticles)

According to the invention, sodium alginate is used to obtain modified alginate, and then to synthesize modified Alginate-mOA (AGO) nanoparticles.

In one example of the invention, alginate is reacted with an aqueous solution of acetic acid. The reaction mixture is neutralized, and then dialyzed against distilled water to remove low-molecular-weight impurities; separated the precipitate by a centrifuge; and lyophilized afterwards.

Then, modified oleic acid (mOA) is synthesized by the method as indicated below. Oleic acid and N-(3-Dimethylaminopropyl)-N'-ethylcarbodiimide hydrochloride (referred to as EDC-HCl) are dissolved in dichloromethane (referred to as DCM) together, and then mixed with ethylenediamine (1.34 mL) in DCM. The reaction mixture is reacted with triethylamine to obtain the crude product, the crude product is mixed with brine ($NH_4Cl_{(aq)}$), and the aqueous phase of the product is extracted with DCM and the organic phase was collected, dried over anhydrous magnesium sulfate, and concentrated under reduced pressure to remove DCM. Next, such crude is added to diethyl ether, sonicated in ultrasonic bath to remove residual oleic acid, and the precipitate is collected by using pumping filter. Finally, diethyl ether is removed under reduce pressure. The white powder for pure modified oleic acid (mOA) is obtained. The scheme of the synthesis of modified oleic acid (mOA) is given below:

alginate salts, and oleic acid-modified alginate, omeg-3-modified alginate, olineic acid-modified alginate.

The pharmaceutical composition according to the present invention can be formulated into a dosage form suitable for oral administration using technology well known to those skilled in the art, which includes, but is not limited to, injections (e.g., sterile aqueous solutions or dispersions), sterile powder, tablets, troches, pills, capsules, and the like.

The pharmaceutical composition according to the present invention can be administered via one or more of the following routes: nasal spraying, intramuscular injection, and subcutaneous injection.

In certain embodiments, the pharmaceutical composition is formulated into a dosage form suitable for oral administration and subcutaneous injection.

The pharmaceutical composition according to the present invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, plasticizer, filling agents, disintegrants, surfactants, and/or thickening agents.

The dosage and the frequency of administration of the pharmaceutical composition according to the invention may

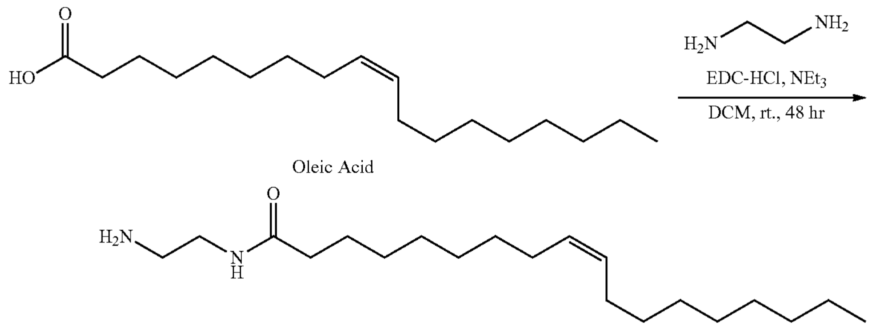

Oleic Acid

Modified Oleic Acid (mOA)

Sodium alginate (0.5 g) was dissolved in water to a concentration of 3.0 wt %. The pH of the solution was adjusted to 3.4 by using 0.4 M HCl. Next, an aqueous solution of EDC-HCl was added slowly to the system, and the pH of the reaction mixture was maintained at 3.4 by the addition of 0.4 M HCl. To prepare different degree of substitution (DS) of AGO, the amount of EDC-HCl (NEDC-HCl/$N_{hexuronic}$=0.2, 0.4, 0.6, 0.8 and 1.0) was 0.096 g, 0.857 g, 0.288 g, 0.383 g, 0.479 g, respectively. After 5 min of reaction, mOA ($N_{amine}$/$N_{hexuronic}$=1.05, in an amount of 0.857 g) was added, and the mixture was stirred uniformly at 35° C. for 24 hr. When the reaction was completed, dialyzed against distilled water for 3 days to remove low-molecular-weight impurities; separated the precipitate which was unreacted mOA by using Centrifuge (9000 rpm, 15 min); and lyophilized subsequently. After lyophilization, residual organic impurities were removed by using Soxhlet extraction with acetone for 3 days. We used vacuum system to remove acetone. Then, we collected a pure light yellow powder for a novel amphiphilic molecule, called as AGO nanoparticles.

Examples of the AGO particles includes a molecule selected from the group consisting of fatty acid-modified vary depending on the following factors: the severity of the disease to be treated, the route of administration, and the weight, age, physical condition and response of the subject to be treated. For instance, the daily dosage of the pharmaceutical composition according to the invention may be 50 mg to 150 mg per $m^2$ of body surface area, and may be administered in a single dose or in several doses daily or weekly-based period.

It is to be understood that both the foregoing general description and the following detailed description are exemplary and explanatory only and are not restrictive of the invention.

The present invention is further illustrated by the following examples, which are provided for the purpose of demonstration rather than limitation.

EXAMPLES

Example 1. Preparation of Remdesivir-Curcumin Containing Nanoparticle 1.0 mg of remdesivir powder (purchased from Selleckchem) and 0.5 mg of curcumin (purchased from Sigma) was dissolved in 0.5 mL of a dimethyl sulfoxide (DMSO) and DI water solution to prepare a remdesivir stock solution having a remdesivir concentration of 20 mg/mL and a curcumin concentration of 10 mg/mL. 5 μL of the remdesivir-curcumin stock solution was added to 95 μL of a DI water solution to obtain a diluted remdesivir-curcumin solution having a remdesivir concentration of 1 mg/mL and a curcumin concentration of 0.5 mg/mL.

0.5 mg of oleic acid-modified alginate (AGO) (i.e. amphiphilic alginate) powder (purchased from Nuecology Biomedical Inc. Canada) was added into an Eppendorf tube, followed by adding 50 μL of the diluted remdesivir-curcumin solution. 0.95 mL of a 1×PBS solution was added into the resulting mixture so as to form 1 mL of a mixture solution (pH 7.4) having an initial AGO concentration of 0.5 mg/mL and an initial free remdesivir concentration of 50 g/mL and free curcumin concentration of 25 μg/mL. The aforesaid procedure was repeated once to form another mixture solution having the same initial AGO concentration and the same initial free remdesivir and curcumin concentration. Subsequently, the two mixture solutions were subjected to stirring at 4° C. for 12 hours, so that two dual-drug AGO nanoparticle solutions were formed.

Example 2. Determination of Drug Encapsulation Efficiency of Remdesivir-Curcumin-Containing AGO Nanoparticle The remdesivir-curcumin-carrying nanoparticle solutions obtained in section A of this example were subjected to determination of drug encapsulation efficiency as follows.

The remdesivir and curcumin stock solutions were subjected to serial dilution to obtain standard remdesivir and curcumin solutions respectively. The standard remdesivir and curcumin solutions were subjected to determination of absorbance using a ultra-high-performance liquid chromatography (UPLC-UV).

Furthermore, each of the remdesivir-curcumin nanoparticle solutions was subjected to centrifugation at 12,000 rpm and 4° C. for 10 minutes. 500 μL of the resulting supernatant was obtained and was added into 500 μL of a DMSO solution so as to form 1 mL of a test solution. Afterward, the test solution was subjected to determination using the HPLC and the test solution was compared to the standard curve so as to determine the unencapsulated remdesivir and curcumin concentration, respectively (i.e. the remaining free drug concentration). The drug encapsulation efficiency of the test solution was calculated using the following equation (1):

$$A=[(B-C)/B]\times 100 \quad (1)$$

A—drug encapsulation efficiency (%)

B=initial free drug concentration

C—unencapsulated drug concentration of respective test solution

The experimental data obtained are expressed as mean±SD (standard deviation) or mean.

The remdesivir-curcumin nanoparticle solutions prepared by 12 hours and 24 hours of stirring respectively had drug encapsulation efficiency of 75.4%±0.35% and 64%±40.25%. In other words, the nanoparticle solutions prepared by 12 hours and 24 hours of stirring respectively had nanoparticle concentrations (i.e. encapsulated remdesivir and curcumin concentrations) of approximately 50.7 μg/mL and 40 μg/mL.

Example 3. Determination of Physical Properties of Nanoparticle According to Present Invention A suitable amount of AGO powder as used in Example 1 was dissolved in 1 mL of a deionized (DI) solution to form an AGO nanoparticle solution having a AGO concentration of 1.0 mg/mL.

The remdesivir-curcumin nanoparticles in the nanoparticle solution with drug encapsulation efficiency of 60-75% and a remdesivir-curcumin nanoparticle concentration of 30 μg/mL, which was obtained in section A of this example, were subjected to conjugation of an anti-ACE 2 antibody. Specifically, 1 μL of an anti-human ACE2 antibody (1 mg/mL in double distilled water) was added to the remdesivir-curcumin nanoparticle solution, followed by stirring at 4° C. for 1 hour. 0.05 mL of a EDC (1-ethyl-3-(3-dimethylaminopropyl)carbodiimide) solution (0.1%, w/v) was added to the resulting solution, followed by being left standing for over 4 hours. Therefore, an anti-human ACE 2 antibody conjugated particle solution containing anti-ACE 2 AGO nanoparticles was formed. The anti-ACE2 antibody conjugated nanoparticle solution was subjected to determination of drug encapsulation efficiency generally according to the method described in this example.

The hydrodynamic diameter of the AGO nanoparticles, the remdesivir-curcumin nanoparticles, and the anti-ACE2 remdesivir-curcumin nanoparticles were measured in double distilled water by virtue of dynamic light scattering (DLS) on BI-200SM Goniometer (Brookhaven Inc., Holtsville, NY).

The zeta potential of the AGO nanoparticles, the remdesivir-curcumin nanoparticles, and the anti-ACE2 remdesivir-curcumin nanoparticles were measured in double distilled water on a laser Doppler anemometry system (Beckman Coulter Inc., USA) to investigate the surface potential of these particles.

In addition, the AGO nanoparticles and the remdesivir-curcumin nanoparticles were observed using Jeol 2100 Transmission Electron Microscope (Jeol Ltd., Japan) under 20,000 magnification, so as to determine the particle size of these particles, and so as to confirm encapsulation of ganetespib by CHC and conjugation of the anti-EGFR antibody. The experimental data obtained are expressed as mean±SD or mean.

The antibody-conjugated nanoparticle solution had drug encapsulation efficiency of 55-70%. In other words, the antibody-conjugated nanoparticle solution approximately had an anti-ACE2 remdesivir-dexamethasone nanoparticle concentration of 35 g/mL.

The hydrodynamic diameter and zeta potential of the AGO nanoparticles, the remdesivir-dexamethasone AGO nanoparticles, and the anti-ACE2 remdesivir-dexamethasone nanoparticles are shown in Table 1 below.

TABLE 1

| Particle | Hydrodynamic diameter (nm) | Zeta potential (mV) |
|---|---|---|
| AGO | 200 | −43 |
| Dual-drug AGO | 320 | −40 |
| anti-ACE2 dual-drug AGO | 380 | −50 |

As shown in Table 1, the hydrodynamic diameter of the remdesivir-dexamethasone nanoparticles was larger than that of the AGO particles, indicating that the both drug were successfully encapsulated by the drug carrier AGO to form a nanoparticle. Furthermore, the hydrodynamic diameter of the anti-ACE2 dual-drug AGO nanoparticles was larger than that of the dual-drug AGO nanoparticles, indicating that the anti-ACE2 antibody was successfully conjugated to the nanoparticle having both remdesivir and curcumin encapsulated by AGO.

In view of the foregoing, AGO can encapsulate both remdesivir and curcumin simultaneously to form a nanoparticle, to which a biologically functional molecule can be further conjugated.

Example 4. Determination of Drug Encapsulation Efficiency of Remdesivir-Dexamethasone-Containing AGO Nanoparticle The remdesivir-dexamethasone-carrying AGO nanoparticle solutions was prepared based on the preparation condition given in Example 2 and were subjected to determination of drug encapsulation efficiency as follows.

The remdesivir and dexamethasone stock solutions were subjected to serial dilution to obtain standard remdesivir and dexamethasone solutions respectively. The standard remdesivir and dexamethasone solutions were subjected to determination of absorbance using a ultra-high-performance liquid chromatography (UPLC).

Furthermore, each of the remdesivir-dexamethasone AGO nanoparticle solutions was subjected to centrifugation at 10,000 rpm and 4° C. for 10 minutes. 500 μL of the resulting supernatant was obtained and was added into 500 μL of a DMSO solution so as to form 1 mL of a test solution. Afterward, the test solution was subjected to determination using the UPLC and the test solution was compared to the standard curve so as to determine the unencapsulated remdesivir and dexamethasone concentration, respectively (i.e. the remaining free drug concentration). The drug encapsulation efficiency of the test solution was calculated using the following equation (1):

$$A = [(B - C)/B] \times 100 \quad (2)$$

A=drug encapsulation efficiency (%)
B=initial free drug concentration
C=unencapsulated drug concentration of respective test solution The experimental data obtained are expressed as mean±SD (standard deviation) or mean.

The remdesivir-dexamethasone AGO nanoparticle solutions prepared by 24 hours of stirring respectively had drug encapsulation efficiency of 71.8%±0.75% and 89.2%±0.54% for remdesivir and dexamethasone respectively, Table 2. In other words, the nanoparticle solutions prepared by 24 hours of stirring respectively had nanoparticle concentrations (i.e. encapsulated remdesivir and dexamethasone concentrations) of approximately 40 μg/mL and 20 μg/mL.

TABLE 2

| Sample | Encapsulation Efficiency (%) |
|---|---|
| AGO/R + Dexamethasone | 71.8 ± 0.75 (RED)<br>89.2 ± 0.54 (DEX) |

Example 5. Drug Release Test of the Remdesivir-Dexamethasone AGO Nanoparticle In vitro drug release tests were conducted by suspending the dual-drug-carrying AGO nanoparticles prepared in Example 4, in PBS at pH 7.4. The suspensions were divided into 1.5 mL Eppendorf tubes. The tubes were gently shaken at 37° C. in an orbital shaker incubator. At predetermined times (4, 8, 12, 24, 36 and 48 h), the released (free) drugs were separated from the drug-loaded nanoparticles by centrifugation. For remdesivir and dexamethasone, samples were centrifuged at 12,000 rpm for 4 minutes and the pellet consisting of the precipitated released remdesivir and dexamethasone was analyzed. The concentrations of remdesivir and dexamethasone were quantified by UPLC. The percentages of remdesivir and dexamethasone released at each time were calculated from the following equation:

$$\text{Released drug (\%)} = \left[(\text{released drug})/(\text{initial amount of drug})\right] \times 100 \quad (2)$$

Drug released profiles are illustrated in FIG. 1 for a time period of 72 hours. It is clear that remdesivir was depleted in about 48 hours, while dexamethasone showed a slower release profile and reached 70% of release over a elution duration of 72 hours. This drug release test indicated both drugs can be co-released with different release kinetics from the as-prepared dual-drug-carrying AGO nanoparticle. This study also shows a potential therapeutic performance with medicinal synergy while the as-prepared nanoparticle is working for anti-viral treatment in-vivo and may be beneficial for clinical translation.

Figure 2:
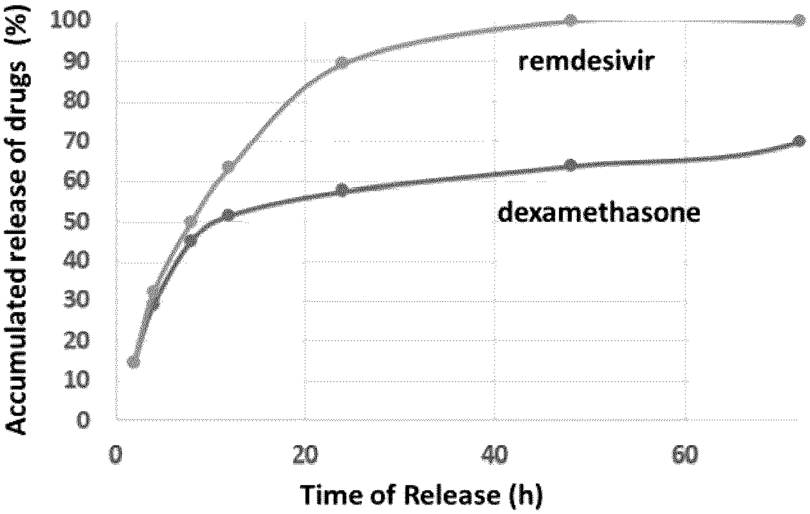
FIG. 2 provides spherical geometry of the dual-drug carrying AGO nanoparticles prepared in Example 4.

Example 6. Structural Morphology of the Remdesivir-Dexamethasone AGO Nanoparticle Morphological structure of the dual-drug AGO nanoparticle was examined using Scanning Electron Microscopy as illustrated in FIG. 2. The as-prepared dual-drug-carrying particles show a spherical geometry with size ranging approximately between 100-250 nm, suggested the self-assembly behavior of the AGO molecules can be efficiently processed under a mild and neutral aqueous solutions with high drug encapsulation efficiency. This finding also suggests the superior processing advantage as compared with traditional high-energy emulsification process such as in the formation of liposome to encapsulate and delivery drugs of interest.

Example 7. In-Vivo Evaluation on the Biosafety of the Remdesivir-Dexamethasone-Carrying AGO Nanoparticles Via Oral Administration (1) Husbandry and test system: All animal experiments and care were approved by the Institutional Animal Care and Use Committee (IACUC) of the Agricultural Technology Research Institute (IACUC No. 109064)

Husbandry: Animals were housed in the AAALAC accredited facility of ATRI. Animals with the same gender and treatment were housed by using polycarbonate cages in the animal room Temperature: 22±4° C.

Relative Humidity: 30~70%

Light Cycle: 12 hours light and 12 hours dark

Diets: Autoclaved laboratory 5053-PicoLab® Rodent Diet 20—LabDiet, Richmond, IN, USA Water: Autoclaved RO water was supplied ad libitum via water bottles attached to the cages Identification: Animals were identified by ear notch and each cage was labeled with cage number, study number, IACUC number, gender, treatment, and animal ID number.

(2) Test system:

Strain and Source: Sprague Dawley strain/BioLASCO Taiwan Co. Ltd.

Age and body weight: Δt study initiation, rats were approximately 8 weeks old, with the body weights range of 177.43 g to 210.66 g prior to dosing Sex/Number: Female/3

Acclimation: Animals were quarantined by GLP animal facility of ATRI. Animal Center and acclimated for 6 days in the testing room before dosing (3) Test Article Preparation: The "AGO" was manufactured and processed according to Example 4. Test article was weighted and mixed with normal saline to be dissolved than diluted to 200 mg/mL before dosing.

(4) Experimental Procedure

The animals were fasted for 16 to 18 hours before the administration, and three to four hours after the administration.

The administration was conducted with a syringe and feeding tubes at the volume of 10 mL/kg base on the body weight measured on the administration day.

Clinical Observation: The animals were observed continuously for 10 minutes after the administration, and observed 30 minutes and four hours after the administration on the administration day. The animals were observed once from 1 to 14 days after the administration.

Measurement of body weight: Body weights were measured 0 (before administration), 7 and 14 days after the administration with an electric balance. Gross necropsy: The survived animals were subjected to a gross necropsy 14 days after the administration. The survived animals were euthanized by bleeding from the abdominal aorta under isoflurane anesthesia. External surface of the body, all orifices, subcutis, cranial, abdominal and pelvic cavities with their contents were observed for all animals.

Blood sampling and Treatment: Blood samples were obtained through abdominal aorta and collected in without the anticoagulants. Serum were harvested by centrifugation in a refrigerated centrifuge at 3,500 rpm for 15 minutes at 4° C. within 1 hours. Each serum samples were stored at −30° C.

Tissue Collecting and Organ Weight Measurements: The heart, lung, spleen, liver, kidney and adrenal gland were removed and weights were measured using an electric balance for all animals. The heart, lung, spleen, liver, kidney and adrenal gland were preserved in 10% neutralized buffered formalin.

Results (1) Mortality/Moribundity: No animal death was observed during the study period.

(2) Clinical observations: No adverse clinical signs were observed in all animals during the study period.

(3) Body Weight: No abnormalities were observed in all animals during the study period.

(4) Gross necropsy findings: On the necropsy day, no abnormal findings were observed in all animals.

(5) Organs weights: Individual animal organ weight were observed and shown in Table 3, and no abnormal growth or change was found.

TABLE 3

| | | Organs weights (g) | | | | | |
|---|---|---|---|---|---|---|---|
| Dose (mg/kg) | Animal No. | Heart | Lung | Spleen | Liver | Kidney | Adrenal gland |
| 2,000 | 1/F | 0.875 | 1.502 | 0.437 | 8.458 | 1.860 | 0.057 |
| | 2/F | 0.916 | 1.498 | 0.500 | 10.476 | 1.994 | 0.059 |
| | 3/F | 0.812 | 1.505 | 0.401 | 8.326 | 1.736 | 0.053 |

Example 8. Histopathological Analysis of the Vital Organs Prepared from Example 7

This study was entrusted by the Nuecology Biomedical Inc. Vancouver, BC, Canada. This study evaluated the pathological changes induced by the test article, Sodium Alginate-mOA (AGO) via oral gavage in female rats. Three female Sprague Dawley rats, 8 weeks old, were oral gavaged AGO at 2,000 mg/kg in double-distilled $H_2O$ solution. All rats were sacrificed on day 14. The heart, kidneys, lungs, liver, and spleen were collected and were submitted for histopathological evaluation. Under histopathological evaluation, no significant lesions of the heart, kidneys, liver, lungs, or spleen were found in the AGO treated females.

In conclusion, the pilot study of acute oral toxicity of at 2,000 mg/kg Sodium Alginate-mOA did not cause significant lesions of the heart, kidneys, liver, lungs, or spleen in female rats according to histopathological examination.

Three female Sprague Dawley rats, 8 weeks old, were oral gavaged Sodium Alginate-mOA (AGO) at 2,000 mg/kg in double-distilled $H_2O$ solution. All rats were sacrificed on day 14.

The heart, kidneys, lungs, liver, and spleen were collected and were submitted for histopathological evaluation (Table 3). Tissues were further processed, embedded in paraffin, cut at 3 μm by microtone stained with Hematoxylin & Eosin (H&E) stain and evaluated under light microscope (BX-53, Olympus, Tokyo, Japan) for histopathological evaluation.

The severity of lesions was graded according to the methods described by Shackelford et al. (Toxicologic Pathology 30: 93-96, 2002). The degree of lesions was graded from one to five depending on severity: 1=minimal (<1%); 2: slight (1-25%); 3=moderate (26-50%); 4=moderately severe (51-75%); 5=severe/high (76-100%). The pathological nomenclature for each organ is listed in Table 4.

TABLE 4

| Organs of female rats were submitted for histopathological examination | | |
|---|---|---|
| Group/sex | Animal code | Submitted samples |
| Female AGO (2,000 mg/kg) | 1, 2, 3 | Heart, kidneys, liver, lungs, spleen |

Test article: Sodium Alginate-mOA (AGO)

Figure 3:
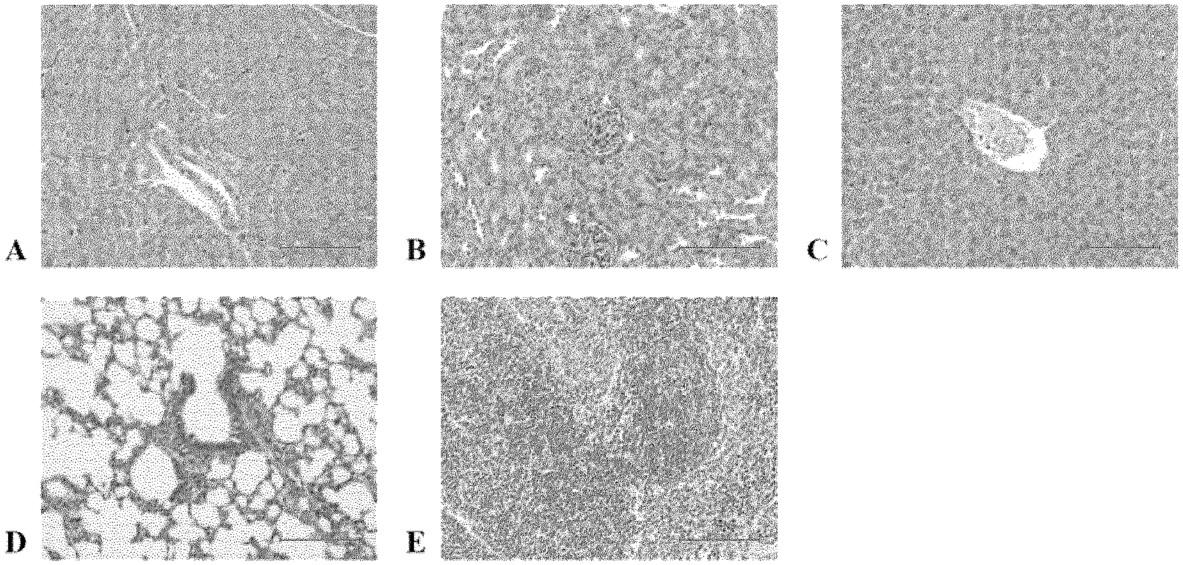
FIG. 3 shows the histopathological findings of the pilot study of acute oral toxicity of sodium alginate-mOA (AGO) in female rats; in which no significant changes of the adrenal glands (A), heart (B), kidneys (C), liver (D), lung (E) and spleen (F) were found in the 2000 mg/kg AGO group (animal code: 1). H&E stain. 400×.

Results:

Histopathological Findings:

Heart, kidneys, liver, lungs, or spleen: No significant lesions of the heart, kidneys, liver, lungs, or spleen were found in the dosage of 2,000 mg/kg AGO treated group (FIG. 3; Table 5).

Conclusion:

Three female Sprague Dawley rats, 8 weeks old, were oral gavaged Sodium Alginate-mOA (AGO) at 2,000 mg/kg in double-distilled $H_2O$ solution. All rats were sacrificed on day 14. The heart, kidneys, lungs, liver, lungs, and spleen were collected and were submitted for histopathological evaluation.

From histopathological evaluation, no significant lesions of the heart, kidneys, liver, lungs, or spleen were found in the AGO 2,000 mg/kg treated female rats. (Table 6).

In conclusion, the pilot study of acute oral toxicity of at 2,000 mg/kg Sodium Alginate-mOA did not cause significant lesions of the heart, kidneys, liver, lungs, or spleen in female rats according to histopathological examination.

Example 9. In-Vivo Evaluation on the Acute Toxicity of the Remdesivir-Carrying ACE2-Coated AGO Nanoparticles Via Subcutaneous Injection Administration The remdesivir-carrying ACE2-coated, AGO nanoparticle solutions was prepared based on the preparation condition given in Example 2 and were subjected to determination of acute toxicity via subcutaneous injection administration in vivo.

15 female ICR mice, 7 weeks old, were divided into 3 groups consisting of dosages of RAGO gel at 7.5 mg/kg (L), 15 mg/kg (M) and 25 mg/kg (H) in aqueous PBS buffer solution via subcutaneous (s.c.) injection in mice. Each group contained five female mice that were given a single administration of the test article via subcutaneous route. The injection volume was 100 uL/20 g body weight. All mice were sacrificed on day 14.

The heart, kidneys, lungs, liver, and spleen were collected and were submitted for histopathological evaluation (Table 8). Tissues were further processed, embedded in paraffin, cut at 3 mm by microtone, stained with Hematoxylin & Eosin (H&E) stain and evaluated under light microscope (BX-53, Olympus, Tokyo, Japan) for histopathological evaluation.

TABLE 5

| Pathological nomenclatures and criteria |
|---|
| Observation fate: |
| Gross finding: |
| No abnormalities (NA) |
| Left (L); Right (R) |
| Bilateral (B) |
| Slight, − |
| Mild, ++ |
| Moderate, +++ |
| Severe, ++++ |
| Histopathological nomenclatures: |
| No significant lesions (NSL) |
| Distribution: Local, Multifocal, Local Extensive and Diffuse |
| Degree[1]: Slight, Moderate, and Severe |
| Duration: Acute, Subacute, and Chronic |
| Exudate: Serous, Fibrinous, and Purulent |
| Modification: Degeneration, Necrosis, . . . |

[1]Severity of lesions was graded according to the methods described by Shackelford et al. (2002) (*Toxicologic Pathology* 30; 93-96, 2002). Degree of lesions was graded from one to five depending on severity: 1 = minimal (<1%); 2 = slight (1-25%); 3 = moderate (26-50%); 4 = moderate/severe (51-75%); 5 = severe/high (76-100%).

TABLE 6

Summary of pathological incidence of rats in the acute oral toxicity test of sodium alginate-mOA (AGO)

| Organ | Histopathological findings | Group RAGO gel (mg/kg) L | M | H |
|---|---|---|---|---|
| Heart | | — | — | •— |
| Kidney | Cyst, tubule, focal, slight | — | — | 1/5 |
| Liver | Fatty change, multifocal, slight | — | 1/5 | •— |
| Lung | Alveolar collapse, artifact, diffuse, slight to moderate severe | 5/5 | 5/5 | 5/5 |
| Spleen | | — | — | — |

L-RAGO gel: 7.5 mg/kg; L-RAGO gel: 15 mg/kg; L-RAGO gel: 25 mg/kg. Test article: Remdesivir loaded AGO gel was single s.c. injected on day 0 and mice were sacrificed after 14 days.
— No effect.
1 Degree of lesions was graded from one to five depending on severiy: 1 = minimal (<1%); 2 = slight (1-25%); 3 = moderate (26-50%); 4 = moderate/severe (51-75%); 5 = severe/high (76-100%).
2 Incidence: Affected mice/Total examined mice (n = 5).

TABLE 7

Pathology-individual micro findings of rats in the acute oral toxicity test of sodium alginate-mOA (AGO)

| Group/ organs | Histo- pathological findings[1] | Animal code 2000 mg/kg 1 | 2 | 3 | / | / | / | / | / | / | / | / | / |
|---|---|---|---|---|---|---|---|---|---|---|---|---|---|
| Adrenal | | — | — | — | / | / | / | / | / | / | / | / | / |
| | | | | | / | / | / | / | / | / | / | / | / |
| | | | | | / | / | / | / | / | / | / | / | / |
| Heart | | — | — | — | / | / | / | / | / | / | / | / | / |
| | | | | | / | / | / | / | / | / | / | / | / |
| | | | | | / | / | / | / | / | / | / | / | / |
| Kidney | | — | — | — | / | / | / | / | / | / | / | / | / |
| | | | | | / | / | / | / | / | / | / | / | / |
| | | | | | / | / | / | / | / | / | / | / | / |
| Liver | | — | — | — | / | / | / | / | / | / | / | / | / |
| | | | | | / | / | / | / | / | / | / | / | / |
| | | | | | / | / | / | / | / | / | / | / | / |
| Lung | | — | — | — | / | / | / | / | / | / | / | / | / |
| | | | | | / | / | / | / | / | / | / | / | / |
| | | | | | / | / | / | / | / | / | / | / | / |
| Spleen | | — | — | — | / | / | / | / | / | / | / | / | / |
| | | | | | / | / | / | / | / | / | / | / | / |
| | | | | | / | / | / | / | / | / | / | / | / |

—: No significant lesions.
[1]: Degree of lesions was graded from one to five depending on severity: 1 = minimal (<1%); 2 = slight (1-25%); 3 = moderate (26-50%); 4 = moderate/severe (51-75%); 5 = severe/high (76-100%).

TABLE 8

Organs of mice were submitted for histopathological examination

| Group/sex | Animal code | Submitted samples |
|---|---|---|
| Female | | Heart, kidneys, liver, lungs, spleen |
| L-RAGO gel (7.5 mg/kg) | 1, 2, 3, 4, 5 | |
| M-RAGO gel (15 mg/kg) | 6, 7, 8, 9, 10 | |
| H-RAGO gcl (25 mg/kg) | 11, 12, 13, 14, 15 | |

Test article: Remdesivir loaded AGO gel was given as a single s.c. injection on day 0.

Test Article: Remdesivir Loaded AGO Gel was Given as a Single s.c. Injection on Day 0.

The severity of lesions was graded according to the methods described by Shackelford et al. (Toxicologic Pathology 30: 93-96, 2002). The degree of lesions was graded from one to five depending on severity: 1=minimal (<1%); 2: slight (1-25%); 3=moderate (26-50%); 4=moderately severe (51-75%); 5=severe/high (76-100%). The pathological nomenclature for each organ is listed in Table 9.

Results:

(1) Histopathological Findings:

Heart, kidneys, liver, lungs, or spleen:

No significant lesions of the heart, kidneys, liver, lungs, or spleen were found in the dosage of 7.5 mg/kg RAGO, 15 mg/kg and 25 mg/kg treated groups (Table 10).

(2) Non-Specific Findings:

Kidney:

Focal tubular cyst

Only one female mouse in the 25 mg/kg RAGO gel group presented focal, slight tubular cysts in the kidneys (FIG. 3A-C). The incidence was 1/5 in the H-RAGO group. No significant treatment-related effect due to the test article was considered in the kidneys (Table 10).

Liver:

Multifocal fatty change

The M-RAGO gel female mice presented multifocal, slight fatty change in the liver (FIG. 1D-F). The incidence was 1/5 in M-RAGO gel mice. No significant treatment-related effect due to the test article was considered in the liver (Table 10).

Lung:

Diffuse artificial alveolar collapse

All of the groups in the RAGO gel treated female mice presented diffuse slight to moderate/severe artificial alveolar collapse in the lungs (FIG. 3G-I). The incidence was 5/5, 5/5, and 5/5 in RAGO gel treated female mice. No significant treatment-related effect due to the test article was considered in the lungs (Table 10).

Conclusion:

15 female ICR mice, 7 weeks old, were divided into 3 groups consisting of dosages of RAGO gel at 7.5 mg/kg (L), 15 mg/kg (M) and 25 mg/kg (H) in aqueous PBS buffer solution via subcutaneous (s.c.) injection in mice. Each group contained five female mice that were given a single administration of the test article via subcutaneous route. All mice were sacrificed on day 14. The heart, kidneys, lungs, liver, lungs, and spleen were collected and were submitted for histopathological evaluation.

From histopathological evaluation, no significant lesions of the heart, kidneys, liver, lungs, or spleen were found in the groups given RAGO gel 7.5 mg/kg (L), 15 mg/kg (M) and 25 mg/kg (H) via subcutaneous (s.c.) injection in female mice. Some non-specific or artificial lesions were found, such as slight tubular cysts in the kidneys; multifocal fatty change in the liver. Diffuse alveolar collapse was observed in the alveolar spaces of the lungs and might be related to improper fixation. No significant treatment-related effects caused by the test article to organs were observed under microscopic examination. These observations are listed in the tables and figures and were considered to be non-specific or artificial lesions and incidental findings.

In conclusion, the toxicity study of Remdesivir loaded AGO gel at dosages of 7.5, 15 or 25 mg/kg via subcutaneous injection in female mice did not cause significant lesions of the heart, kidneys, liver, lungs, or spleen in mice, according to histopathological examination.

TABLE 9

| Pathological nomenclature and criteria |
|---|
| Observation fate: |
| Gross finding: |
| No abnormalities (NA)<br>Left (L); Right (R)<br>Bilateral (B)<br>Slight, +<br>Mild, ++<br>Moderate, +++<br>Severe, ++++<br>Histopathological nomenclature: |
| No significant lesions (NSL)<br>Modification: Degeneration, Necrosis, . . .<br>Distribution: Focal, Multifocal, Local Extensive and Diffuse<br>Degree: Minimal, Slight, Moderate, Moderate/Severe and Severe/High<br>Duration: Acute, Subchronic, and Chronic<br>Exudate: Serous, Fibrinous, and Purulent |

1 Severity or lesions was graded according to the methods described by Shackelford et al. (2002) (*Toxicologic Pathology* 30: 93-96, 2002). Degree of lesions was graded from one to five depending on severity: 1 = minimal (<1%); 2 = slight (1-25%); 3 = moderate (26-50%); 4 = moderate/severe (51-75%); 5 = severe high (76-100%).

TABLE 10

Summary of pathological incidence of toxicity study of Remdesivir loaded AGO gel via subcutaneous injection in mice

| | | Group RAGO gel (mg/kg) | | |
|---|---|---|---|---|
| Organ | Histopathological findings | L | M | H |
| Heart | | — | — | — |
| Kidney | Cyst, tubule, focal, slight | — | — | 1/5 |
| Liver | Fatty change, multifocal, slight | — | 1/5 | — |
| Lung | Alveolar collapse, artifact, diffuse, slight to moderate/severe | 5/5 | 5/5 | 5/5 |
| Spleen | | — | — | — |

L-RAGO gel: 7.5 mg/kg; L-RAGO gel: 15 mg/kg; L-RAGO gel: 25 mg/kg. Test article: Remdesivir loaded AGO gel was single s.c. injected on day 0 and mice were sacrificed after 14 days.

— No effect.

1 Degree of lesions was graded from one to five depending on severity: 1 = minimal (<1%); 2 = slight (1-25%); 3 = moderate (26-50%); 4 = moderate/severe (51-75%); 5 = severe/high (76-100%).

2 Incidence: Affected mice/Total examined mice (n = 5).

Example 10. Preparation of Remdesivir-Curcumin Containing AGO™ Nanoparticle 1.0 mg of remdesivir powder (purchased from Selleckchem) and 0.5 mg of Methotrexate (MTX, purchased from Sigma) was dissolved in 0.5 mL of a dimethyl sulfoxide (DMSO) and DI water solution, respectively, to prepare a remdesivir stock solution having a remdesivir concentration of 20 mg/mL and a MTX concentration of 10 mg/mL. 5 μL of the remdesivir-Methotrexate stock solution was added to 95 μL of a DI water solution to obtain a diluted remdesivir-Methotrexate solution having a remdesivir concentration of 1 mg/mL and a Methotrexate concentration of 0.5 mg/mL.

0.5 mg of oleic acid-modified alginate (AGO™) (i.e. amphiphilic alginate) powder (from Nuecology Biomedical Inc. Canada) was added into an Eppendorf tube, followed by adding 50 μL of the diluted remdesivir-Methotrexate solution. 0.95 mL of a 1×PBS solution was added into the resulting mixture so as to form 1 mL of a mixture solution (pH 7.4) having an initial AGO™ concentration of 0.5 mg/mL and an initial free remdesivir concentration of 40 μg/mL and free Methotrexate concentration of 40 μg/mL. The aforesaid procedure was repeated once to form another mixture solution having the same initial AGO™ concentration and the different ratios of initial free remdesivir and Methotrexate concentration (Table 11). Subsequently, the two mixture solutions with drug concentration ratios ranging from 1:1, 2:1, to 5:1, were subjected to stirring at 4° C. for 12 hours, so that a dual-drug AGO™ nanoparticle solutions were formed.

TABLE 11

Remdesivir-MTX Dual-drug system with various starting Remdesivir to MTX ratios for a subsequent AGO encapsulation.

| Sample | Remdesivir | Methotrexate |
|---|---|---|
| 1:1 | 40 μg/ml | 40 μg/ml |
| 2:1 | 40 μg/ml | 20 μg/ml |
| 5:1 | 40 μg/ml | 8 μg/ml |

After those two drugs encapsulated into AGO™ nanoparticle, the resulting physical properties of the dual-drug AGO™ nanoparticle were characterized in terms of zeta potential and particle size as listed in Table 12.

TABLE 12

Remdesivir-MTX dual-drug encapsulation into AGO ™ nanoparticle to form a dual-drug nanocarrier with zeta potential and average particle size (as determined using Dynamic Light Scattering Analyzer)

| Sample REM:MTX | Zeta potential (mV) | Size (nm) |
|---|---|---|
| 1:1 | −31.8 ± 1.2 | 898 ± 218 |
| 2:1 | −20.3 ± 0.6 | 785 ± 207 |
| 5:1 | −21.4 ± 1.3 | 646 ± 137 |

The “absolute” zeta potential of the resulting remdesivir-MTX AGO™ nanoparticle illustrated a range from 20-32 mV, indicating the dual-drug carrying AGO™ nanoparticle possessing a high colloidal stability in the aqueous-based solution, such as in saline, blood, body fluid. This suggest a potential use for medical uses for anti-viral purpose. Besides, the resulting dual-drug AGO™ nanoparticles show a size ranging from 650-~900 nm, which is also suitable for a number of administration routes, included IV injection, SC injection, oral, and nasal spraying, etc.

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment.

What is claimed is:

1. A nanoparticle comprising: a first anti-viral drug, and a second anti-viral drug; and an alginate-oleic acid particle, wherein the first anti-viral drug and the second anti-viral drug are encapsulated in said alginate-oleic acid particle, the particle has a particle size ranging from 50 nm to 300 nm, and the particle comprises oleic acid-modified alginate that has a structure of Formula I and Formula II:

Formula I

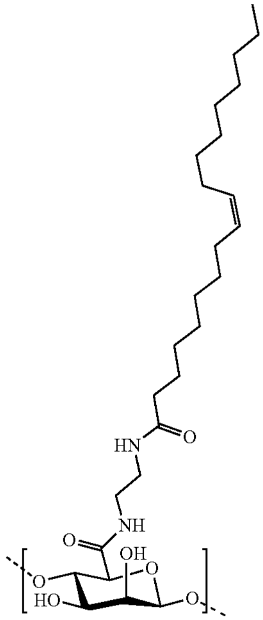

;

Formula II

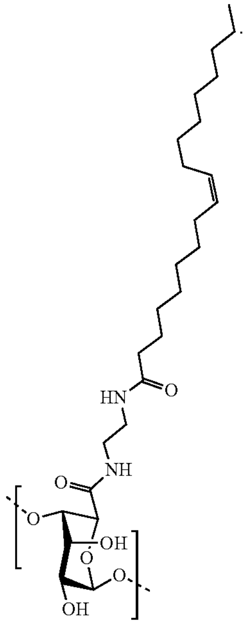

.

2. The nanoparticle of claim 1, wherein the first anti-viral drug is remdesivir.

3. The nanoparticle of claim 1, wherein the second anti-viral drug is an autophagy inhibitor, a protease inhibitor, an antibiotic, or a plant drug.

4. The nanoparticle of claim 1, wherein the second anti-viral drug is selected from the group consisting of Favipiravir, Hydroxychloroquine, Carfilzomib, Darunavi, Pitavastatin, Lamivudine, Lopinavir, Nelfinavir, Ritonavir, Darunavir, Ledipasvir, Telaprevir, Rosuvastatin Calcium, Atovaquone, Moexipril, Moexipril, Azithromycin, Curcumin, artemisinin and combinations thereof.

5. The nanoparticle of claim 1, which is a remdesivir-curcumin particle.

6. The nanoparticle of claim 1, wherein the alginate-oleic acid particle is conjugated on a surface of the particle with a human Angiotensin-converting enzyme 2 (ACE2) antibody.

7. A pharmaceutical composition comprising the nanoparticle as defined in claim 1.

8. The pharmaceutical composition of claim 7, comprising the first anti-viral drug and the second anti-viral drug, wherein the first anti-viral drug is remdesivir, and the second anti-viral drug is curcumin.

9. The pharmaceutical composition of claim 7, which is effective against coronavirus.

10. The pharmaceutical composition of claim 7, which is effective against SARS-CoV-2.

11. The pharmaceutical composition of claim 8, which is effective against coronavirus.

12. The pharmaceutical composition of claim 8, which is effective against SARS-CoV-2.

13. A method for treatment of a virus infection in a subject, comprising:

administering to the subject a pharmaceutical composition comprising the nanoparticle as defined in claim 1.

14. The method of claim 13, wherein the virus is coronavirus.

15. The method of claim 13, wherein the virus is SARS-CoV-2.

16. The nanoparticle of claim 1, wherein the alginate-oleic acid particle has a particle size ranging from 50 nm to 100 nm.

* * * * *